US00PP36677P2

(12) United States Plant Patent
Hansen

(10) Patent No.: US PP36,677 P2
(45) Date of Patent: May 13, 2025

(54) ***PHLOX* PLANT NAMED 'Pink Lightning'**

(50) Latin Name: *Phlox paniculata*
Varietal Denomination: Pink Lightning

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,959

(22) Filed: Apr. 16, 2024

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

(56) References Cited

PUBLICATIONS etsy.com/shop/SherwoodGrowers (retrieved online Aug. 20, 2024) (Year: 2023).*

* cited by examiner

*Primary Examiner* — Susan McCormick Ewoldt
*Assistant Examiner* — Zachariah Allan Kay

(57) ABSTRACT

A unique cultivar of Tall *Phlox* plant named 'Pink Lightning' is characterized by vigorous, dense, upright, highly branched peduncles, with dark-green, lanceolate leaves. Flowering begins in mid-July and continues for up to about six weeks in cooler weather conditions, on heavily-branched peduncles, and completely covers the top of the plant in peak season. Flower petals are bright deep pink with a white starburst eye. The new plant shows excellent powdery mildew resistance. The new plant is especially suitable for a cut flower, for the landscape as a potted plant, and in the garden as a specimen or en masse.

2 Drawing Sheets

Botanical classification: *Phlox paniculata.*
Variety denomination: 'Pink Lightning'.

STATEMENT REGARDING PRIOR DISCLOSURES UNDER 37 CFR 1.77(B)(6)

The claimed plant was first offered for sale privately by Walters Gardens, Inc. on Apr. 1, 2024, to Prides Corner Farms. Walters Gardens, Inc. obtained the plant and all information relating thereto, from the inventor. No plants of *Phlox* 'Pink Lightning' have been sold in this country or anywhere in the world, nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct cultivar of Tall *Phlox* plant known as *Phlox* 'Pink Lightning' and will be referred to hereafter by its cultivar name or the "new plant". The new plant was hybridized by the inventor in the outdoor trial beds of a wholesale perennial nursery in Zeeland, Michigan on Jul. 6, 2017, as a cross between a proprietary, unreleased hybrid of *Phlox paniculata* assigned the breeder code 14-668-1 (not patented) as the female or seed parent and the proprietary, unreleased hybrid known only by the breeder code 14-591-1 (not patented) as the male or pollen parent. The new plant passed initial evaluation in the summer of 2019 and was assigned the breeder code 17-35-x through the remaining evaluation process.

'Pink Lightning' was first asexually propagated by division at the same nursery in Zeeland, Michigan in the fall of 2019 with later propagation by cuttings and shoot tip tissue culture. The unique characteristics of the new plant have been found to be reproducible and stable in successive generations by all the above methods of asexually propagated and the resultant plants have been found to be identical to the original selection.

BRIEF SUMMARY OF THE PLANT

*Phlox* 'Pink Lightning' is unique from all other Tall *Phlox* known to the inventor. The nearest comparison plants known to the inventor include: the female and male parents, 'Glamour Girl' U.S. Plant Pat. No. 25,778, 'Bartwelve' U.S. Plant Pat. No. 11,804, 'Sunset Coral' U.S. Plant Pat. No. 35,222, 'Prismatic Pink' U.S. Plant patent application Ser. No. 18/445,125, and 'Bright Eyes' (not patented).

The female parent has a shorter habit, the foliage is narrower, the flowers are more cupped and more lavender-pinkish with fewer flowers per inflorescence. The male parent has a taller habit, wider leaves and the flowers are light pink with a dark pink eye.

'Glamour Girl' has flowers that are flowers of hot coral-pink with darker eye. 'Bartwelve' has a smaller habit and smaller inflorescences with fewer flowers that are a medium pink with a dark pink eye. 'Sunset Coral' has a similar habit with flowers that are coral-pink with a tinge of orange. 'Prismatic Pink' has bubblegum pink flowers with a dark pink eye. 'Bright Eyes' has a taller habit, is more susceptible to powdery mildew, has smaller inflorescences, and the flowers are lighter pink with a dark pink eye.

*Phlox* 'Pink Lightning' differs from all other *Phlox* known to the inventor in the following repeatedly observed traits in combination:

1. Vigorous plants of dense upright habit, producing tall, clean, dark-green, glabrous, lanceolate leaves;
2. Multiple lightly-branched stems produce heavily-branched panicles;
3. Flower beginning in mid-July and continuing for up to six weeks, in cool conditions, completely covering the plant at peak flowering;
4. Flowers are bright deep pink with a white starburst eye;
5. Foliage is highly resistant to powdery mildew in conditions that would normally be exhibited on partially susceptible cultivars.

BRIEF DESCRIPTION OF THE DRAWINGS

The photographs of the new plant demonstrate the unique traits of *Phlox* 'Pink Lightning' and the overall appearance of the two-year-old plant growing in a full-sun display garden in Zeeland, Michigan. The colors in the drawings are as accurate as reasonably possible with color reproductions. Variations in ambient light spectrum, source, and direction may cause the appearance of minor variations in color.

DETAILED BOTANICAL DESCRIPTION

Figure 1:
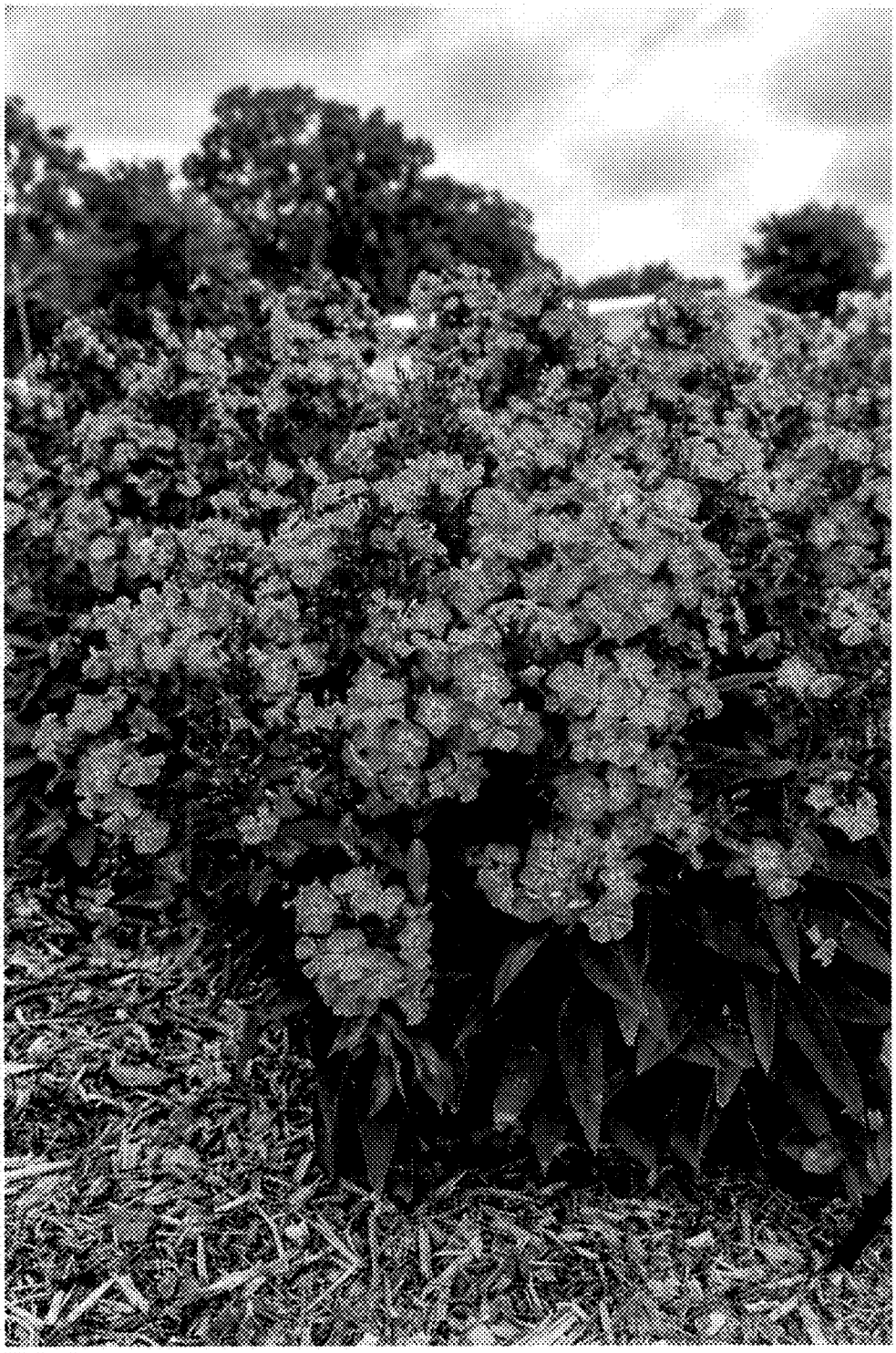
FIG. 1 shows a landscape habit view of the new plant in peak flower.
Figure 2:
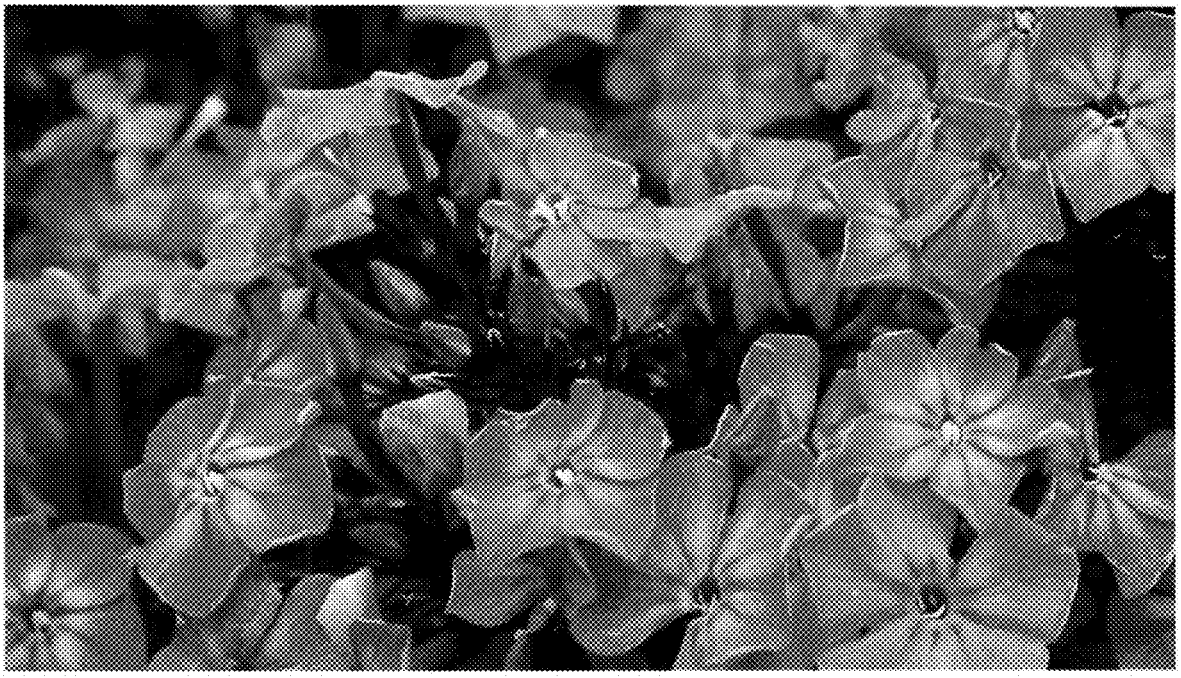
FIG. 2 shows a close-up of the flowers and buds.

The following descriptions and color references are based on the 2015 edition of The Royal Horticultural Society Colour Chart except where common dictionary terms are used. *Phlox* 'Pink Lightning' has not been observed in all possible environments. The phenotype may vary slightly with different growing environments such as temperature, light, fertility, soil pH, moisture, and maturity levels, but without any change in the genotype. The following observations and size descriptions are based on two-year-old plants in a partially shaded greenhouse or a full-sun trial garden of a wholesale perennial nursery in Zeeland, Michigan with supplemental fertilizer and water as needed.

Botanical classification: *Phlox paniculata;*

Parentage: Female or seed parent is 14-668-1; male or pollen parent is 14-591-1;

Plant habit: Winter-hardy, evergreen herbaceous perennial; dense, producing about 16 stiff, upright stems; flowering to about 84 cm tall and 65 cm wide;

Propagation: Stem cuttings; rooting in about 3 weeks;

Time to produce a finished crop in 3.8-liter pots: About 8 to 10 weeks; vigorous;

Root: Fibrous and freely branching; color creamy white to tan depending on soil type;

Leaves: Simple; opposite; lanceolate; apex narrowly acute; base attenuate; margin micro-dentate to ciliolate; adaxial sparsely micro-puberulent and matte, abaxial glabrous and lustrous; to about 90 mm long by about 40 mm wide, average about 80 mm long and 32 mm wide;

Leaf color: Adaxial expanding between RHS 146D and RHS 144A, abaxial nearest RHS 146C; mature adaxial between RHS NN137A and RHS NN137B and mature abaxial between RHS 137B and RHS N138B; with faint anthocyanin expression;

Foliage fragrance: None detected;

Veins: Pinnate; convergent near leaf margin; glabrous adaxial and abaxial, midrib about 1.5 mm wide at base; slightly impressed adaxial and costate abaxial;

Vein color: Adaxial midrib and primary veins nearest RHS 146B; abaxial midrib nearest RHS 145C, and primary and secondary veins nearest RHS 137B;

Petiole: Flattened; glabrous adaxial and abaxial; about 2 mm long and 2 mm wide;

Petiole color: Variable; between RHS 145C and RHS 146D proximally where protected from direct light and distally and nearest RHS N186C where exposed to high light;

Stems: Cylindrical; stiff; upright; glabrescent, to puberulent distally; branching below flowers; to about 82 cm long and 13 mm diameter near base, average about 75 cm long and 11 mm diameter at base;

Stem color: Variable; proximal portion RHS 146D with slightly-raised longitudinal striations of nearest RHS 161B; distal portion nearest RHS 146B with strong anthocyanin expression of nearest RHS N186C;

Nodes: 20 nodes before flowers; average about 2.5 cm apart, greater proximally;

Node color: Color nearest RHS 146B proximally and distally nearest RHS 146B with moderate to strong blush of nearest RHS N186C;

Inflorescence: Upright; with 15 distally branched nodes; densely flowering in about the upper 20 cm and to about 21 cm wide; about 400 to 600 flowers per branched stem;

Flowers: Perfect; salverform; mostly flat faced; to about 31 mm across face and 31 mm tall; with fused corolla tube about 27 mm long, 4 mm diameter near face, and 2 mm diameter at base; attitude upright to outwardly;

Flower longevity: About 5 days on plant; self-cleaning;

Flowering season: Beginning in mid-July for up to about six weeks;

Flower fragrance: Lightly sweet;

Buds one to two days prior to opening: Narrowly clavate; acute apex with rounded base; petals implicate; abaxial corolla tube puberulent, bulb and calyx glabrous;

Bud size: About 31 mm long, bulb to about 11 mm long and 5 mm diameter near middle; corolla tube portion to about 21 mm long and 4 mm diameter below bulb and base of corolla about 2 mm diameter;

Bud color: Exposed petal bulb portion between RHS 55B and RHS N57D; corolla tube portion between RHS 70C and RHS 68D with distal striations nearest RHS 71C; calyx nearest RHS 137C with white translucent margins nearest RHS NN155C, and moderate anthocyanin blushing of nearest RHS N79B in center and RHS 61A along margin;

Petals: Typically five; consisting of limb and basal claw fused into corolla tube; limb obdeltoid; apex rounded, margin entire; limbs imbricate about 10 percent; limb glabrous adaxial and abaxial, adaxial corolla tube pubescent in proximal 4 to 6 mm and glabrous distally, abaxial corolla tube puberulent; slightly cupped producing a sinuate flower face;

Petal size: Limb about 13 mm long and 16 mm wide near middle; tube about 26 mm long and 4 mm diameter near face and 2 mm diameter near base;

Petal color upon first opening:

*Adaxial.*—Limb with center 1 mm wide eye nearest RHS NN155B, next distal 1 mm ring nearest RHS NN74C and margins nearest RHS 71A, middle one-third to one-half nearest RHS NN155D, distal one-half nearest RHS 67C; corolla tube basal 5 mm nearest RHS 145D and distal portion between RHS 70B and RHS NN155D.

*Abaxial*.—Limb distal two-thirds between RHS 67C and RHS 67D with center nearest RHS 76C with margins nearest RHS 71A; corolla tube basal 3 mm between RHS 145C and RHS 145D, distal portion nearest RHS N75B.

Petal color upon maturity:

*Adaxial*.—Limb with center 1 mm wide eye nearest RHS NN155B, next distal 1 mm ring nearest RHS NN74C and margins nearest RHS 71A, middle one-third to one-half between RHS 76B and RHS 76C, distal one-half nearest RHS 67C; corolla tube basal 5 mm nearest RHS 145D and distal portion between RHS 70B and RHS NN155D.

*Abaxial*.—Limb nearest RHS 76B, distal corolla tube between RHS 77B and RHS N77B.

Androecium: Five;

*Filaments*.—Five, adnate to inner corolla to various heights about 20 mm to 25 mm from base; free in the distal 1 mm and 0.2 mm in diameter.

*Filament color*.—In free portion nearest RHS NN155D, where fused nearest RHS 75B.

*Anther*.—Five; oblong ellipsoidal; dorsifixed; longitudinal; about 3 mm long by 1 mm wide; color nearest RHS 11D.

*Pollen*.—Nearly microscopic; color nearest RHS 18C.

Gynoecium: One pistil per flower; 26 mm long;

*Style*.—Cylindrical; about 23 mm long and 0.3 mm diameter when the flower is mature; persistent after flower abscission; color nearest RHS 71A.

*Stigma*.—Typically, trifid in proximal 1 mm long; about 0.3 mm diameter; color nearest RHS 1C.

*Ovary*.—Superior; conical; glabrous; lustrous; acute apex and truncate base; about 2.5 mm long and 1.2 mm diameter at base; color nearest RHS 143A.

Calyx: Campanulate; to about 10 mm long and 5 mm across at apex;

Sepals: Five; linear; adaxial and abaxial slightly lustrous; narrowly acute apex, fused in basal 5 mm, free in distal 5 mm; margin entire; individually about 10 mm long and 1.7 mm wide at fusion;

Sepal color: Adaxial and abaxial nearest RHS 137C with white translucent margins nearest RHS NN155C, and moderate anthocyanin blushing of nearest RHS N79B in center and RHS 61A along margin;

Peduncle: Glabrous; stiff; upright; cylindrical; highly branched; to 25 cm long and 8 mm diameter below branches; with up to 15 branches at about a 45-degree angle above horizontal, branches to about 2.5 mm diameter at base and 16 cm long;

Peduncle color: Nearest RHS 146C with variably strong to moderate blush of nearest RHS N186C;

Pedicel: Cylindrical; micro-puberulent; flexible; upright to outwardly; arcuate slightly upwardly on outer flowers, straight on inner flowers; to about 4 mm long and 1 mm diameter;

Pedicel color: Nearest RHS 146B with light blush of nearest RHS N186C;

Fruit and seed have not been observed;

Hardiness and culture: The new plant grows best with full sun, light moisture, and deep drainage; hardy in at least USDA zone 3 through 8.

Disease and pest resistance: *Phlox* 'Pink Lightning' demonstrates excellent powdery mildew resistance from various species in the order *Erysiphales* under conditions that would normally show symptoms. No pest resistance or susceptibility beyond that common for *Phlox* has been observed.

I claim:

1. A new and distinct cultivar of Tall *Phlox, Phlox* plant named 'Pink Lightning', as herein described and illustrated.

* * * * *